United States Patent [19]

Klemm

[11] Patent Number: Plant 5,277

[45] Date of Patent: Sep. 4, 1984

[54] CARNATION NAMED "KLEREPOLA"

[76] Inventor: Siegfried Klemm, Hanfacker 9, 7000 Stuttgart 50, Fed. Rep. of Germany

[21] Appl. No.: 401,962

[22] Filed: Jul. 26, 1982

[51] Int. Cl.[3] ..... A01H 5/00
[52] U.S. Cl. ..... Plt./73
[58] Field of Search ..... Plt./73

*Primary Examiner*—James R. Feyrer
*Attorney, Agent, or Firm*—Chas. W. Rummler

[57] ABSTRACT

A new variety of carnation plant distinguished by the bright red coloration of its medium sized blooms which are borne on sturdy pedicels carried by long, strong peduncles and by its continuous and abundant production of flowers.

1 Drawing Figure

BACKGROUND OF THE NEW PLANT

This carnation cultivar originated as a sport of the unpatented cultivar named "Ministar" and was discovered by me on May 5, 1975, in a field of the parent variety growing in my greenhouse at Stuttgart, West Germany. The bright red and attractive coloration of this flower sport led me to propagate it by means of cuttings to determine its characteristics as an independent plant. Propagation of this new cultivar was done in my greenhouse at Stuttgart, West Germany, and was carried through several successive generations which demonstrated that the new plant not only retained the desirable growing and production characteristics of its parent, but also that its novel characteristics hold true from generation to generation and appear to be firmly fixed.

DESCRIPTION OF THE DRAWING

My new carnation plant is illustrated by the accompanying full color photographic drawing, which allows the inflorescence of a fully grown plant, the view including buds in various stages of opening, as well as fully opened flowers, the color rendition being as nearly true as it is possible to obtain by means of conventional photographic procedures.

DESCRIPTION OF THE NEW PLANT

The following is a detailed description of my new carnation cultivar based upon observation of plants grown under conventional greenhouse procedures, the color designations being according to The H.C.C. Color Chart by Robert F. Wilson issued by The British Colour Council in collaboration with The Royal Horticultural Society of London, England.

THE PLANT

Origin: Sport.
Parentage: Minister (unpatented).
Classification: Botanic —*Dianthus caryophyllus.* Commercial — Spray carnation.
Form: Bush.
Height: About 90 to about 140 cm.
Growth: Vigorous and upright with moderate strength.
Branching: Normal.
Foliage:
- *Quantity.*—Moderate.
- *Leaf size.*—Moderate.

- *Leaf shape.*—Oblong with entire margins.
- *Texture.*—Smooth.
- *Color.*—Upper side — Blue-Green. Under side — Blue-Green.

THE BUD

Size: Medium, about 15 mm. in diameter and about 38 mm. long.
Form: Generally ovoid, becoming cylindrical when opening.
Opening Rate: Moderate.
Color: When sepals first divide — Yellow-Green. When petals begin to unfurl — Yellow-Green.
Sepals:
- *Condition.*—Upstanding.
- *Color.*—Inside — Grey-Green. Outside — Yellow-Green with White tips.

Calyx:
- *Shape.*—Cylindrical.
- *Size.*—Moderate, about 16 mm. broad and about 18 mm. long.
- *Splitting.*—The calyx does not split.
- *Aspect.*—Smooth.

Peduncle: Rigid and erect.
- *Color.*—Grey-Green.

THE FLOWER

Blooming habit: Continuous and profuse.
Size of bloom: Medium. Diameter — about 50 to 55 mm. Depth — about 30 mm.
Borne: Singly on strong, upright pedicels.
Shape: Flat upon opening and this form does not change.
Petalage: Number of petals — about 32.
- *Arrangement.*—Generally imbricated.
- *Shape.*—Fan-shaped with serrated margins.
- *Color.*—Outer and inside petals — HCC 819 to 819/1. Reverse side — HCC 819 to 819/1.

Texture: Soft.
Appearance: Shiny.
Peduncle: Sturdy and upright.
- *Length.*—About 45 cm.
- *Color.*—Grey-Green.

Persistence: The flowers hang on and dry.
Fragrance: None.
Lasting quality:
- *On plant.*—About 14 days.
- *As a cut flower.*—About 10 days.

REPRODUCTIVE ORGANS

Stamens: Anthers and pollen are rarely present.
Pistils: No more than 3 in number.

*Length.*—About 36 mm.

*Stigmas.*—Color — Cream White to Light Pink.

Fruit: Fertile.

*Shape.*—Cylindrical.

*Color.*—Green/Brown at maturity.

I claim:

1. A new and distinct carnation cultivar, substantially as herein shown and described, characterized by its high productivity of bright red flowers borne singly on rigid, upright pedicels carried in spray arrangement on long, strong peduncles.

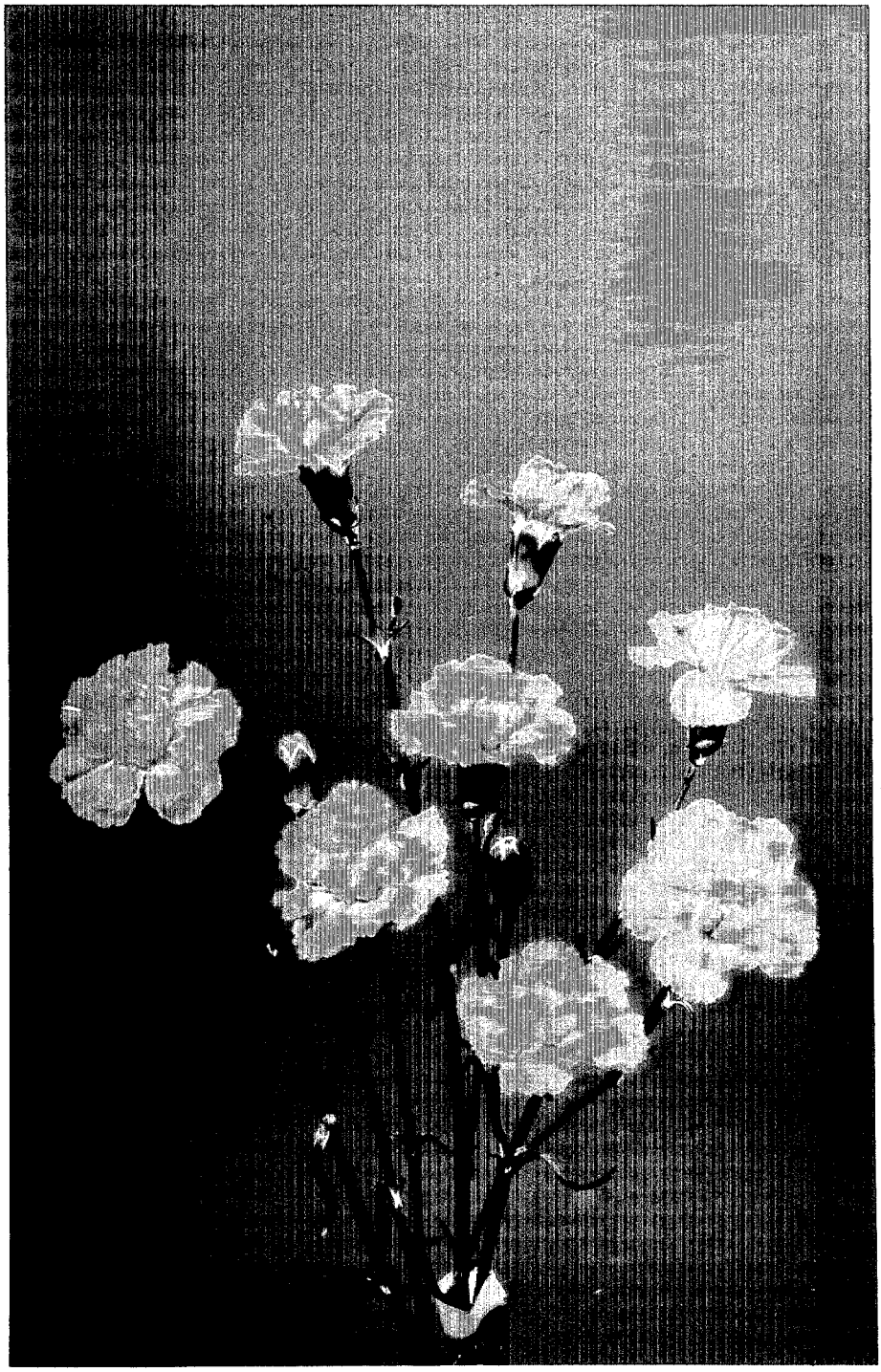

* * * * *